(12) United States Patent
Fung et al.

(10) Patent No.: US 8,905,989 B2
(45) Date of Patent: Dec. 9, 2014

(54) TAMPON WITH SEGMENTED GROOVES

(71) Applicant: McNeil-PPC, Inc., Skillman, NJ (US)

(72) Inventors: Paul Y. Fung, South River, NJ (US); Dmitry Yavich, Brooklyn, NY (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 13/851,191

(22) Filed: Mar. 27, 2013

(65) Prior Publication Data
US 2013/0211364 A1 Aug. 15, 2013

Related U.S. Application Data

(63) Continuation of application No. 12/581,388, filed on Oct. 19, 2009, now Pat. No. 8,460,262.

(51) Int. Cl.
*A61F 13/20* (2006.01)

(52) U.S. Cl.
CPC ......... *A61F 13/2071* (2013.01); *A61F 13/2034* (2013.01); *A61F 13/2051* (2013.01); *Y10S 604/904* (2013.01)
USPC ...................................... 604/385.17; 604/904

(58) Field of Classification Search
CPC ............ A61F 13/2002; A61F 13/2005; A61F 13/2008; A61F 13/2011; A61F 13/2017; A61F 13/202; A61F 13/2022; A61F 13/2025; A61F 13/2028; A61F 13/2031; A61F 13/2034; A61F 13/2037; A61F 13/2054; A61F 13/206; A61F 13/2065; A61F 13/2088; A61F 13/2091; A61F 13/2094; A61F 13/2071; A61F 13/2077
USPC ............... 604/385.17, 385.18, 378–380, 904, 604/11–18; 424/431; 28/118
See application file for complete search history.

(56) References Cited

U.S. PATENT DOCUMENTS

| | | |
|---|---|---|
| 2,798,260 A | 7/1957 | Niepmann et al. |
| 3,422,496 A | 1/1969 | Wolff et al. |
| 4,816,100 A | 3/1989 | Friese |
| 5,374,258 A | 12/1994 | Lloyd et al. |
| 5,458,835 A | 10/1995 | Wilkes et al. |
| 5,832,576 A | 11/1998 | Leutwyler et al. |
| 5,909,884 A | 6/1999 | Schwankhart |

(Continued)

FOREIGN PATENT DOCUMENTS

| | | |
|---|---|---|
| DE | 40502965-0001 | 10/2005 |
| DE | 40502965-0002 | 10/2005 |

(Continued)

OTHER PUBLICATIONS

Wikipedia, Aug. 15, 2012, Wikipedia (internet) p. 1.

(Continued)

*Primary Examiner* — Lynne Anderson
*Assistant Examiner* — Bradley Philips

(57) ABSTRACT

An intravaginal tampon is formed of compressed material and has an outer surface, an insertion end, a withdrawal end, and a center portion formed between the insertion and withdrawal ends. The outer surface has at least two segmented grooves are formed therein, and each segmented groove is separated from and spaced at a distance from an adjacent segmented groove. Each segmented groove has at least one substantially longitudinal segment and at least one accumulator segment. The arrangement of the segments provides a pooling region to impede bodily fluid flow along the outer surface of the tampon.

18 Claims, 10 Drawing Sheets

(56) References Cited

U.S. PATENT DOCUMENTS

| | | | |
|---|---|---|---|
| 5,911,712 A | 6/1999 | Leutwyler et al. | |
| 6,310,269 B1 | 10/2001 | Friese et al. | |
| D477,075 S | 7/2003 | Schoelling | |
| 7,311,699 B2 * | 12/2007 | Carlin | 604/355 |
| 7,549,982 B2 * | 6/2009 | Carlin | 604/385.18 |
| 8,029,485 B2 * | 10/2011 | Jensen | 604/385.17 |
| 2002/0151859 A1 | 10/2002 | Schoelling | |
| 2005/0113784 A1 | 5/2005 | Jensen | |
| 2005/0113785 A1 | 5/2005 | Jensen | |
| 2005/0113787 A1 | 5/2005 | Carlin | |
| 2005/0113788 A1 | 5/2005 | Carlin | |
| 2005/0113789 A1 | 5/2005 | Jensen | |
| 2005/0113807 A1 | 5/2005 | Carlin | |
| 2007/0083182 A1 | 4/2007 | Schoelling | |
| 2008/0200892 A1 | 8/2008 | Van Ingelgem et al. | |

FOREIGN PATENT DOCUMENTS

| | | | |
|---|---|---|---|
| DE | 40502965-0003 | 10/2005 | |
| DE | 40502965-0004 | 10/2005 | |
| DE | 40502965-0005 | 10/2005 | |
| DE | 40502965-0006 | 10/2005 | |
| DE | 40502965-0007 | 10/2005 | |
| DE | 40502965-0008 | 10/2005 | |
| DE | 40502965-0009 | 10/2005 | |
| DE | 40502965-0010 | 10/2005 | |
| EP | 1108408 A | 6/2001 | |
| EP | 1125570 A | 8/2001 | |
| EP | 1459720 | * 10/2003 | A61F 13/20 |
| EP | 1459720 A | 9/2004 | |
| EP | 1481656 A | 12/2004 | |
| EP | 1383453 B | 8/2006 | |
| JP | 2004089576 A | 3/2004 | |
| WO | WO 02/078586 A | 10/2002 | |
| WO | WO 2008/095937 A | 8/2008 | |
| WO | WO 2009/129910 A | 10/2009 | |

OTHER PUBLICATIONS

Math Open Reference, Aug. 15, 2012, Math Open Reference (internet) p. 1.

* cited by examiner

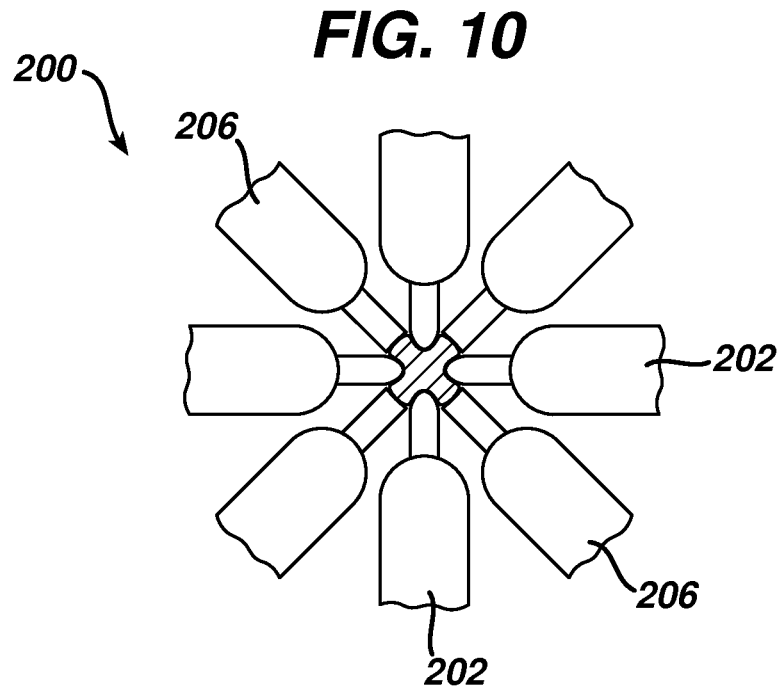
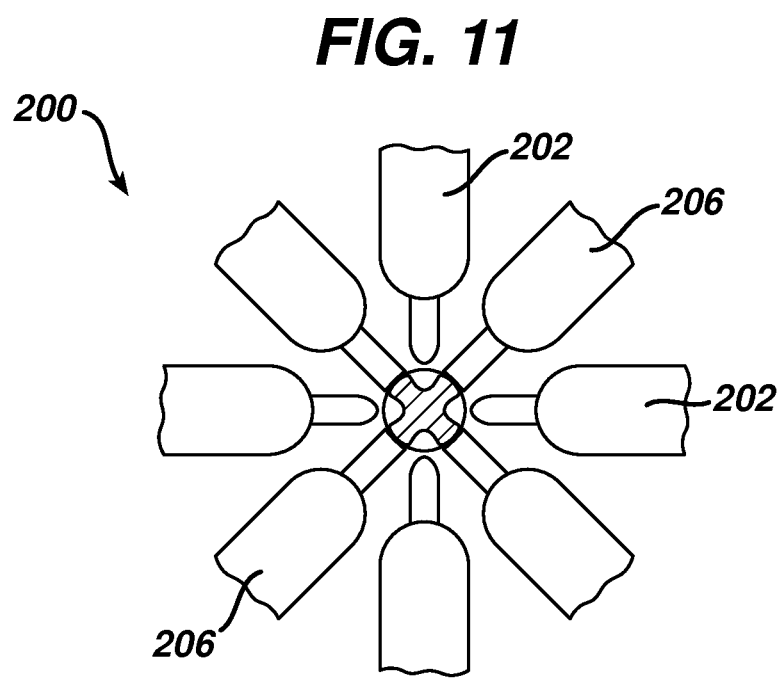

TAMPON WITH SEGMENTED GROOVES

This application is a continuation of U.S. patent application Ser. No. 12/581,388 filed on Oct. 19, 2009, the complete disclosure of which is hereby incorporated herein by reference for all purposes.

FIELD OF THE INVENTION

The present invention relates to intravaginal devices (e.g., tampons) for capturing and storing bodily fluid.

BACKGROUND OF THE INVENTION

Devices for capturing and storing bodily fluid intravaginally are commercially available and known in the literature. Intravaginal tampons are the most common example of such devices. Commercially available tampons are generally compressed cylindrical masses of absorbent fibers that may be over-wrapped with an absorbent or nonabsorbent cover layer.

The tampon is inserted into the human vagina and retained there for a time for the purpose of capturing and storing intravaginal bodily fluids, most commonly menstrual fluid. As intravaginal bodily fluid contacts the tampon, it should be absorbed and retained by the absorbent material of the tampon. After a time, the tampon and its retained fluid is removed and disposed, and if necessary, another tampon is inserted.

There are many brands of tampons commercially available. In general, tampons are split into two categories, those contained and delivered into the body by an applicator and those which are digitally inserted. The tampon of the present invention may be utilized by both delivery means although it is especially appropriate for it to be digitally inserted.

In particular, the tampon of the present invention is formed by processes and apparatus as described in U.S. Pat. No. 6,310,269 (Friese et al.) and U.S. Pat. No. 5,832,576 (Leutwyler et al.). The tampons formed by these processes have center cores which are highly compressed, resulting in densified cores having sufficient column strength required for digital insertion. The area surrounding the core is less dense and has inwardly open grooves, which increase the circumferential surface area of the tampon. The grooves may be straight and aligned parallel to the longitudinal axis or may be of an at least partially helical nature as disclosed in EP 1383453 (Schoelling). In this patent, the shaped, pressed longitudinal grooves increase the surface area, increase the distance the body fluid has to travel and increase the dwell time of the liquid in the at least partially helical grooves. This allows for better absorption and expansion capacity of the tampon than longitudinal, straight grooves.

Other examples of grooves may be found in U.S. Pat. Pub. 2008/0200892, EP 1481656 and WO 2008/095937 (all to Van Ingelgem et al.), EP 1459720 (Schmidt), and U.S. Pat. Pub. 20070083182 (Schoelling). Additionally, tampons having recessed portions such as those in U.S. Pat. Pubs. 20050113784, 20050113785, and 20050113789 (all to Jensen). These recessed portions may be arranged in patterns such as diagonal lines, straight lines, checkerboard and mixtures thereof.

While the invention of helical or other non-linear grooves has increased the absorption of fluid and helped prevent tampon failure, there still remains a need to direct fluid over the outer surface of the tampon. Too often, tampons fail without becoming saturated. This is especially evident when the user removes the tampon and only one side of the tampon has expanded due to fluid absorption.

SUMMARY OF THE INVENTION

Surprisingly, we have found a novel way to improve a tampon's ability to absorb bodily fluids and to reduce by-pass leakage by providing a pooling region. In one aspect of the invention, an intravaginal tampon is formed of compressed material and has an outer surface, an insertion end, a withdrawal end, and a center portion formed between the insertion and withdrawal ends. The outer surface has at least two segmented grooves are formed therein, and each segmented groove is separated from and spaced at a distance from an adjacent segmented groove. Each segmented groove has at least one substantially longitudinal segment and at least one accumulator segment. The substantially longitudinal segment has a substantially longitudinal orientation, and the accumulator segment has a substantially circumferential orientation, and it intersects the at least one longitudinal segment at an angle of less than about 110°.

In another aspect of the invention, an intravaginal tampon is formed of compressed material and has an outer surface, an insertion end, a withdrawal end, and a center portion formed between the insertion and withdrawal ends. The outer surface has at least two segmented grooves are formed therein, and each segmented groove is separated from and spaced at a distance from an adjacent segmented groove. Each segmented groove has at least one substantially longitudinal segment and at least one accumulator segment. The at least one substantially longitudinal segment has a substantially longitudinal orientation, a first end disposed toward the insertion end of the tampon, and a second end disposed toward the withdrawal end of the tampon. The at least one accumulator segment has a first end disposed toward the withdrawal end of the tampon that is joined to second end of the at least one substantially longitudinal segment and a second end, opposite the first end. The second end of the accumulator segment is disposed toward the insertion end of the tampon.

BRIEF DESCRIPTION OF THE DRAWING

FIGS. 8-11 show a cross-section of a tampon press useful for forming a tampon according to the present invention.

DETAILED DESCRIPTION OF THE INVENTION

As used herein the specification and the claims, the term "groove" and variants thereof relate to an indention into the surface of the tampon. Regions between grooves may take the form of ribs.

As used herein the specification and the claims, the term "longitudinal axis" and variants thereof relate to an axis that runs from the insertion end to the withdrawal end substantially through the center of the tampon.

As used herein the specification and the claims, the term "segmented groove" and variants thereof relate to a groove formed in the outer surface of the tampon that has a plurality of discernible elements defined by angles.

As used herein the specification and the claims, the term "longitudinal segment" and variants thereof relate to a groove segment that is oriented substantially in a longitudinal direction, although this could be inclined with respect to the longitudinal axis, e.g., helically. A plurality of longitudinal segments distributed along a segmented groove enables the groove to extend over a substantial portion of the length of the tampon to form a "segmented longitudinal groove."

As used herein the specification and the claims, the term "accumulator segment" and variants thereof relate to a groove segment that, alone or in conjunction with an adjacent groove segment that impedes continuous fluid flow along the length of the tampon.

As used herein the specification and the claims, the term "discernible angle" and variants thereof relate to an angle of less than about 135° formed between adjacent groove segments joined at a vertex. This term includes right angles and acute angles.

Thus, the present invention relates to a tampon with reduced opportunity for bodily fluid to flow along the surface without being absorbed into the absorbent tampon structure. This is accomplished by providing segmented grooves having at least one longitudinal segment and at least one accumulator segment. The at least one accumulator segment is oriented substantially circumferentially about the tampon and/or cooperates with an adjacent groove segment to form a pooling region, which will be further described below. Thus, not only does the present invention provide tampons with a plurality of separate, spaced-apart, elongate, longitudinal grooves, recognized by the prior art as providing improved fluid handling characteristics, but it also provides areas of the outer surface of the tampon that impede continuous bodily fluid flow along the length of the tampon. For example, the discernible angle can both increase the length of the groove and impedes smooth flow of a bodily fluid along the groove. The orientation of a plurality of accumulator segment in adjacent spaced-apart, segmented grooves may also provide a circumferential zone of increased fiber densification.

Figure 1:
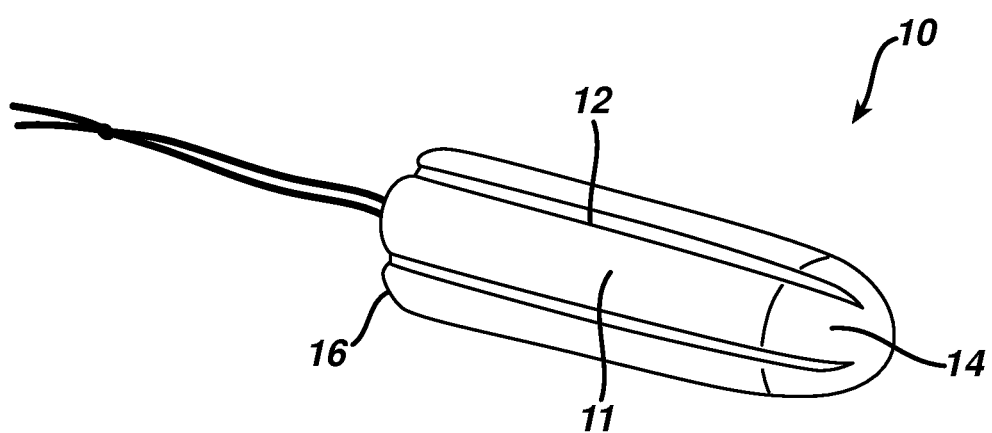
FIG. 1 shows a perspective view of a commercial tampon having longitudinal groove.

Turning to the drawings, FIG. 1 shows a conventional prior art digital tampon 10 having ribs 11 separating longitudinal grooves 12 extending from the insertion end 14 of tampon 10 to the withdrawal end 16. These types of tampons have been commercially available for many years.

Figure 2:
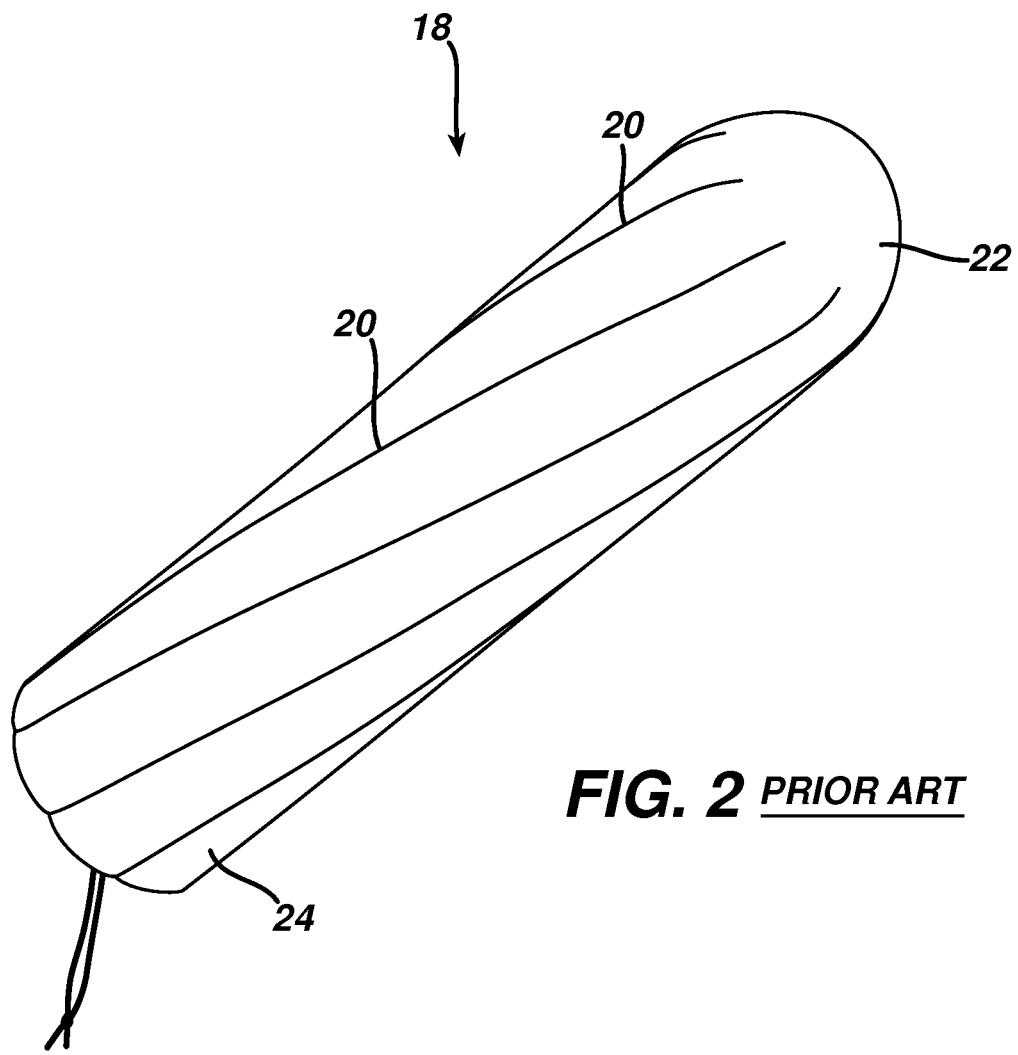
FIG. 2 shows a perspective view of a commercial tampon having spiral or helical grooves.

FIG. 2 shows an example of a spiral or helical groove as described in EP 1383453, U.S. Ser. No. 10/104,264, the disclosures of which are hereby incorporated in their entirety by reference. As indicated in FIG. 2, separate, spaced-apart grooves 20 extends from the insertion end 22 of tampon 18 to the withdrawal end 24. The helical longitudinal grooves 20 are inclined with respect to the longitudinal axis and extend over a circumferential angle α of up to at least 150° of the tampon 18 (as shown in EP 1383453). Tampons having these types of grooves are commercially available from McNEIL-PPC, Inc., Skillman, N.J., USA, under the O.B.® brand.

Figure 3:
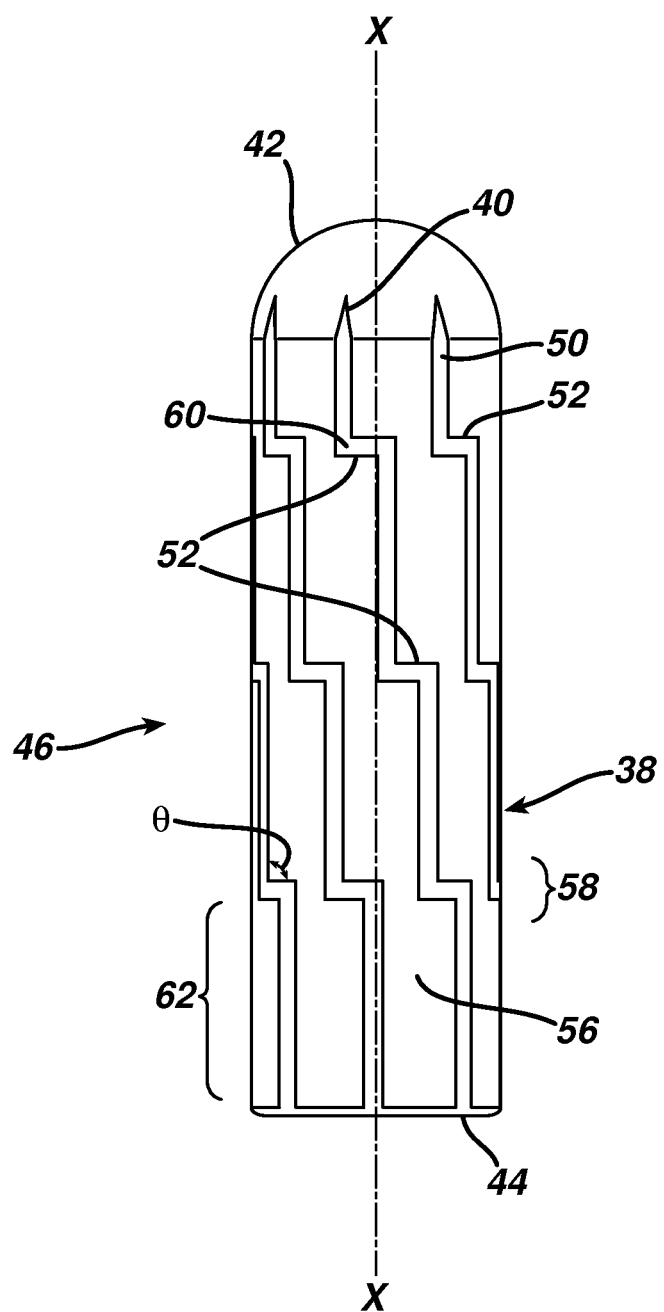
FIG. 3 shows a plan view of a tampon of the present invention having a plurality of segmented grooves.

FIG. 3 shows one embodiment of the present invention. In this example, tampon 38 has an insertion end 42, a withdrawal end 44 and a center portion 46 therebetween. Longitudinal axis is shown as line X-X. As shown in the figure, a segmented longitudinal groove 40 extends from insertion end 42 to withdrawal end 44. Groove 40 contains at least one longitudinal segment 50 and at least one accumulator segment 52 joined to each other at vertex 60. This intersection and the substantial circumferential orientation of the accumulator segment 52 provides one area of the outer surface of the tampon that impedes the flow of bodily fluids along the length of the tampon. For example, a bodily fluid such as menses that contacts longitudinal segment 50 proximate the insertion end and runs down toward the withdrawal end would have its motion impeded by accumulator segment 52. This impediment is more than just redirection along a gentle curve or large, obtuse angle approaching 180° as known in the prior art. It is believed that it is sufficient to cause temporary pooling or accumulation of bodily fluid to enhance localized penetration of the bodily fluid into the absorbent structure of the tampon.

The segmented groove may have additional longitudinal segments 50 and accumulator segments 52 to generally extend the length of the tampon. These additional segments may form a series of "steps" joined by vertices. In the most basic form of the invention, at least one step or discernible angle is formed in at least two separated segmented grooves. In other embodiments, a plurality of more than two separated segmented grooves is formed, each having a series of discernible angles. These segmented grooves may be equally spaced about the circumference of the tampon, or they may have variable spacing.

Figure 4:
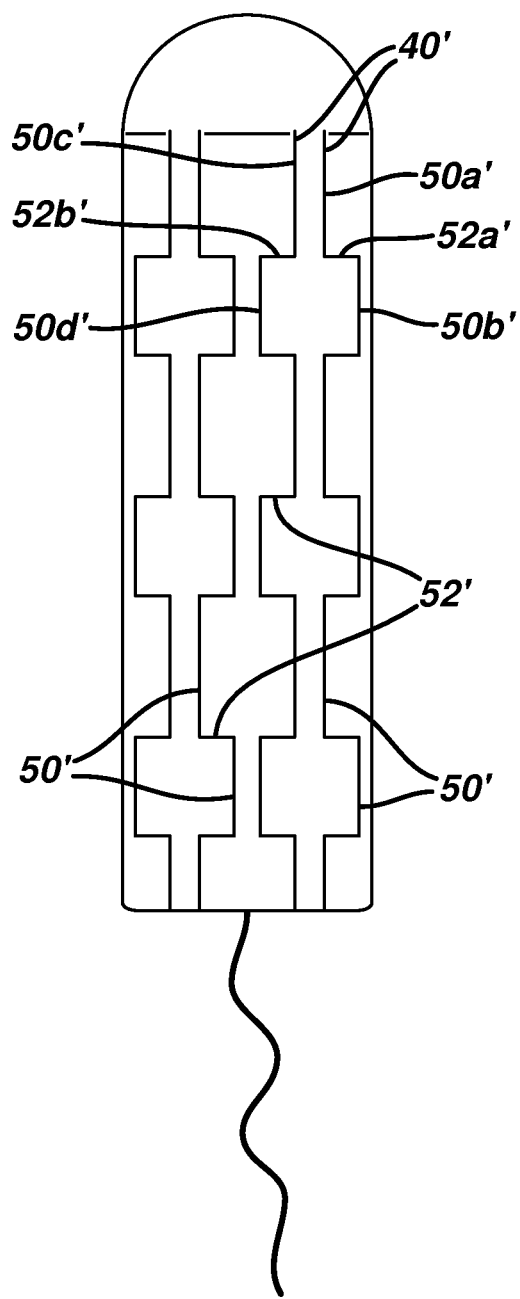
FIG. 4 shows a plan view of an alternate embodiment of a tampon having mirrored segmented grooves.

One example of a tampon having a plurality of variably spaced segmented grooves is shown in FIG. 4. This embodiment has adjacent segmented grooves 40' formed of longitudinal segments 50' and accumulator segments 52' that mirror each other, providing closely spaced longitudinal segments and more distantly spaced longitudinal segments. In particular, a first substantially longitudinal segment 50a' of a first of the at least two segmented grooves 40' is connected to a second substantially longitudinal segment 50b' through a first accumulator segment 52a'. An adjacent, first substantially longitudinal segment 50c' of an adjacent segmented groove is connected to an adjacent, second substantially longitudinal segment 50d' through an adjacent, first accumulator segment 52b'. Thus, the first substantially longitudinal segment 50a' of the first segmented groove and the adjacent, first substantially longitudinal segment 50c' of the adjacent segmented groove are spaced at a first circumferential distance, and the second substantially longitudinal segment 50b' of the first segmented groove and the adjacent, second substantially longitudinal segment 50d' of the adjacent segmented groove are spaced at a second circumferential distance, different than the first circumferential distance. As shown in FIG. 4, this second circumferential distance is greater than the first circumferential distance. A further pair of longitudinal segments of the adjacent segmented grooves can be spaced the first circumferential distance, and further pairs can be spaced at the second circumferential distance or at other circumferential distances. As shown in the embodiments of FIGS. 3 and 4, one type of discernible angle is substantially a right angle or 90°.

Figure 5:
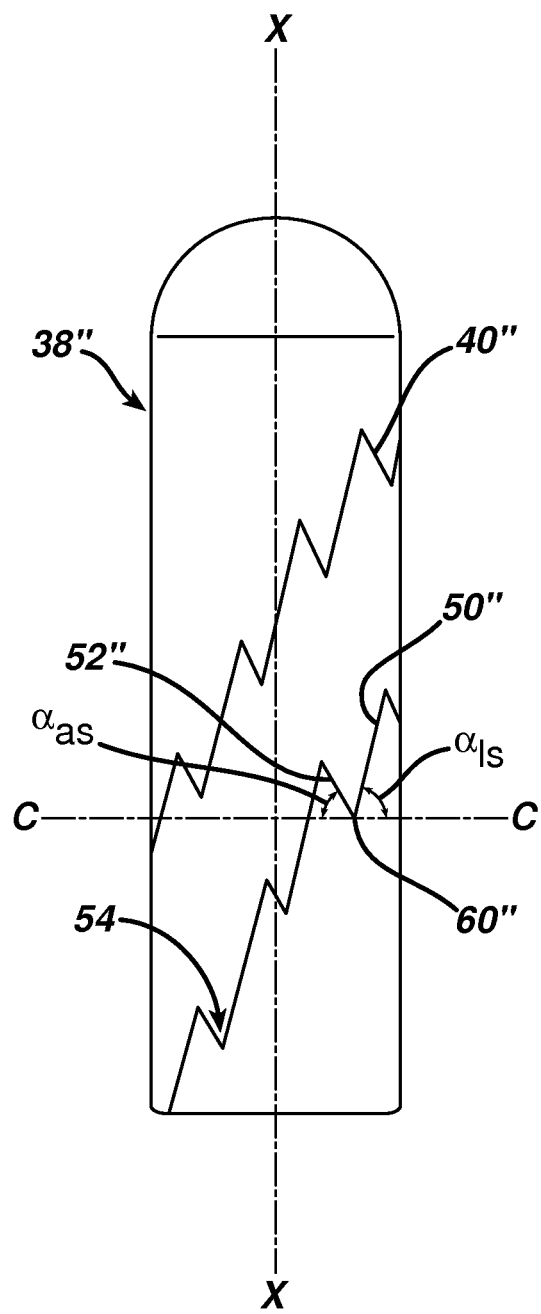
FIG. 5 shows a plan view of still another alternate embodiment of a tampon having inclined segmented grooves.
Figure 6:
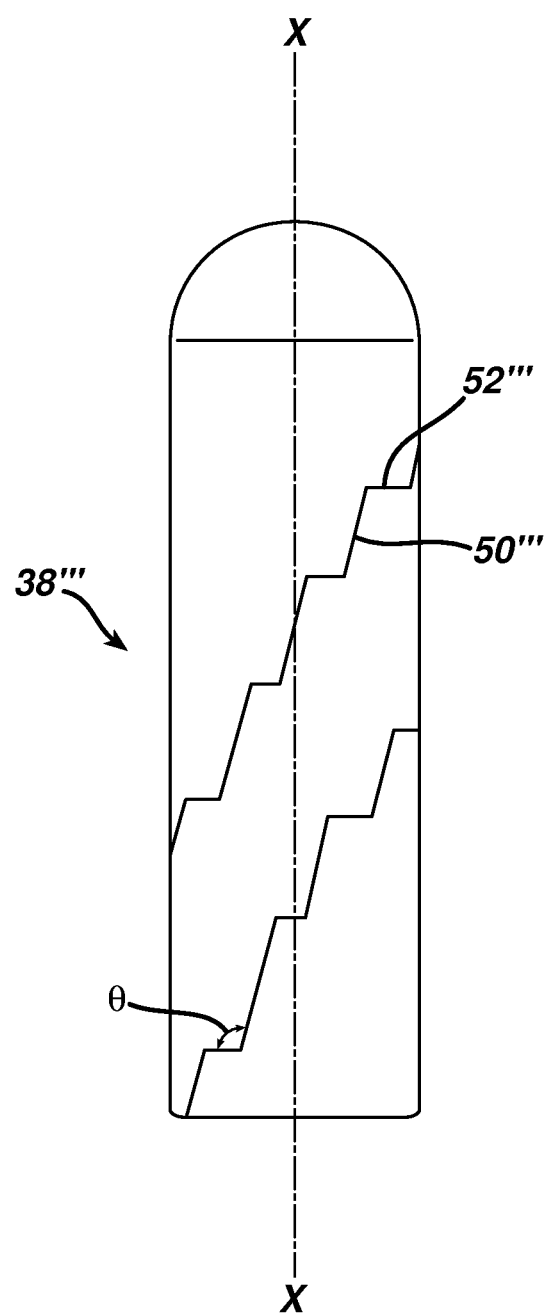
FIG. 6 shows a plan view of still another alternate embodiment of a tampon of the present invention.

Alternatively, the angle between the segments may be acute or slightly obtuse provided it forms a discernible angle θ. Preferably, the discernible angle θ is less than about 135°, more preferably, less than about 110°, even more preferably, less than about 100°. Thus, if a first longitudinal segment is oriented parallel to the longitudinal axis, and an adjacent accumulator segment intersects at an acute angle, this accumulator segment will be inclined toward the insertion end of the tampon. In one example of such an embodiment, the groove resembles a lightning bolt and is shown in FIG. 5. This arrangement of a longitudinal segment 50" and an adjacent inclined accumulator segment 52″ provides two upwardly directed segments extending from their intersection (vertex 60″) at a lower point on the tampon to form a pooling region 54 to enhance pooling along the segmented groove. In another embodiment (shown in FIG. 6), at least one accumulator segment 52′″ is directed substantially circumferentially about the outer surface of the tampon 38′″. An adjacent longitudinal segment 50′″ may be inclined from the longitudinal axis X-X, for example, helically oriented. While the embodiment of FIG. 6 has a slightly obtuse discernible angle θ, both embodiments of FIGS. 5 and 6 will impede fluid flow.

The angle of incline from the longitudinal axis can be identified by a helix angle α, the angle between the helical segment and a circumferential line C-C on the surface of the tampon 38″ as shown in FIG. 5. Thus a groove segment having a helix angle of 0° would be oriented along the circumference of a substantially cylindrical tampon, while a groove segment having a helix angle of 90° would be parallel to the longitudinal axis of a substantially cylindrical tampon. In FIG. 5, a first longitudinal segment 50″ has a helix angle, $α_{ls}$, of about 75°, while an adjacent accumulator segment 52″ has a helix angle, $α_{as}$, of about 45°. In contrast, the longitudinal segments 50 of FIG. 3 have a helix angle of about 90°, while the adjacent accumulator segments 52 have a helix angle of about 0°. Preferably, the longitudinal segments have a helix angle, $α_{ls}$, of at least about 45°, and more preferably, at least about 75°. Preferably, the accumulator segments have a helix angle, $α_{as}$, of less than about 25°, and more preferably, less than about 10°. Alternatively, the sum of the helix angle can be measured. Preferably, the sum of the longitudinal segment helix angle, $α_{ls}$, and the accumulator segment helix angle, $α_{as}$, is at least about 70°, and more preferably, at least about 90°.

Referring to FIG. 3, the outer surface of the tampon is at least partially provided with longitudinal ribs 56 defined by the pressed segmented grooves 40, which generally extend in the axial direction between the insertion end 42 and the withdrawal end 44. The number of longitudinal ribs can vary, for example depending on the diameter of the tampon and/or the type of absorbent material. Preferably, there are at least about four ribs, and more preferably, at least about six. While the present invention, like many known tampons, may have an even number of ribs, it is also possible to produce tampons according to the present invention with an odd number of ribs.

By selective placement of the grooves and their alignment to the longitudinal axis X-X, it is possible to provide areas having different densities resulting from different fiber compression. For example, FIG. 3 shows a series of accumulator segments 52 spaced at regular intervals about the circumference of the tampon 38. As shown, accumulator segment 52 is approximately perpendicular to the longitudinal axis X-X. Likewise, a second segmented groove, located adjacent to the first segmented groove, has a similar pattern of discernible angles and contains longitudinal and accumulator segments 50 and 52, respectively. By having accumulator segments 52 aligned generally circumferentially it is possible to create a region 58 having increased density as compared to that region 62 between longitudinal segments 50. Without being bound to any theory, it is thought that fluid contacting the surface of tampon 38 would be rapidly absorbed inwardly in the regions 62 defined by longitudinal segments 50 as these regions 58 are less dense. The fluid would then be wicked either upward or downward to the more dense regions defined by accumulator segments 52. Preferably, the region 58 is a cylindrical segment having a height of less than about 3 mm, more preferably, having a height of less than about 2 mm.

The absorbent tampons of the present invention include elongate masses of compressed materials, preferably substantially cylindrical masses of compressed materials having a central axis and a radius that defines the outer circumferential surface of the tampon. Tampons are often formed by first obtaining a shaped mass of materials called a tampon blank. This blank can be in the form of a roll of a nonwoven web, a mass of randomly or substantially uniformly oriented material, and the like.

The tampons also have surface features, e.g., grooves, that improve the absorption of fluid and help to prevent early tampon failure in the form of bypass leakage. Further improvements in these properties can be achieved by providing well-defined angles in the grooves, such as right angles and/or acute angles to provide surface features to delay the movement of fluid lengthwise along the surface of the tampon.

These grooves impede a bodily fluid moving lengthwise along the surface of the tampon and provide greater opportunities for the liquid to be absorbed into the tampon structure. In addition, the angles have vertices (not smooth transitions between groove segments) and/or accumulator segments that impede the smooth movement of the bodily fluid along the tampon surface. It is believed that the system of grooves having the discernible angle and groove orientation of the present invention provides improved liquid absorption into the tampon.

The tampon blank is an open structure that is relatively uncompressed and has a relatively low density. It is then compressed to form a product having smaller dimensions and a higher density than the tampon blank. After the tampon is released from compression, it relaxes (or expands), slightly, to its final dimensions. The compressed tampons may have a generally uniform density throughout the tampon, or they may have regions of differing density as described in the commonly assigned patents to Friese et al., U.S. Pat. No. 6,310,269, and Leutwyler et al., U.S. Pat. No. 5,911,712, the disclosures of which are herein incorporated by reference. As shown in FIG. 1, tampons 10 also usually include a cover 12 or some other surface treatment and a withdrawal string or other removal mechanism.

The tampon may have a relatively dense core substantially surrounding its central axis and a less dense annulus surrounding the core and forming the outer circumferential surface. This density differential may be provided by relatively uniform, yet distinct, absorbent material distribution within the core and annulus, or it may be provided by a plurality of ribs which extend radially from the core.

The materials that may be used in the tampon include fibers, foams, and particles or other discrete materials. The tampon includes cellulosic fibers. A useful, non-limiting list of useful cellulosic fibers includes natural fibers such as cotton, wood pulp, jute, hemp, sphagnum, and the like; and processed materials including cellulose derivatives such as regenerated cellulose (including rayon and lyocell), cellulose nitrate, carboxymethyl cellulose, and the like. The tampons may also include other materials including, without limitation, polyester, polyvinyl alcohol, polyolefin, polyamine, polyamide, polyacrylonitrile, and the like.

Preferably, the tampons are formed predominantly of fibers. The fibers may be any of the materials listed above, and may have any useful cross-section, including multi-limbed and non-limbed. Multi-limbed, regenerated cellulosic fibers have been commercially available for a number of years. These fibers are known to possess increased specific absorbency over non-limbed fibers. Commercial examples of these fibers are Galaxy® trilobal viscose rayon fibers available from Kelheim Fibres GmbH Kelheim, Germany, and Viscostar® trilobal viscose rayon fibers available from Lenzing AG, Lenzing, Austria. These fibers are described in detail in Wilkes et al, U.S. Pat. No. 5,458,835, the disclosure of which is hereby incorporated by reference.

Preferably, the tampon blank is substantially enclosed by a fluid-permeable cover. Thus, the cover encloses a majority of the outer surface of the tampon. This may be achieved as disclosed in Friese, U.S. Pat. No. 4,816,100, the disclosure of which is herein incorporated by reference. In addition, either or both ends of the tampon may be enclosed by the cover. Of course, for processing or other reasons, some portions of the surface of the tampon may be free of the cover. For example, the insertion end of the tampon and a portion of the cylindrical surface adjacent this end may be exposed, without the cover to allow the tampon to more readily accept fluids.

The cover can ease the insertion of the tampon into the body cavity and can reduce the possibility of fibers being separated from the tampon. Those of ordinary skill in the art will recognize covers that are useful in conjunction with the tampons of the present invention. They may be selected from an outer layer of fibers which are fused together (such as by thermobonding), a nonwoven fabric, an apertured film, or the like.

Tampons are generally categorized in two classes: applicator tampons and digital tampons, and a certain amount of dimensional stability is useful for each type of tampon. Applicator tampons use a relatively rigid device to contain and protect the tampon prior to use. To insert the tampon into a body cavity, the applicator is partially inserted into the body cavity, and the tampon can be expelled therefrom. In contrast, digital tampons do not have an applicator to help guide them into the body cavity and require sufficient column strength to allow insertion without using an applicator. This strength can be determined by securing one end of the tampon to the fixed plate of a Instron Universal Testing Machine, available from Instron Corporation, Canton, Mass., U.S.A. The moveable plate is brought to contact the opposite end of the tampon and is then set to compress the tampon at a rate of about 5 cm/minute. The force exerted on the tampon is measured continuously, and the point at which this force begins to fall instead of rise is the point at which the tampon buckles. The maximum force achieved is the tampon stability. Preferably, digital tampons of the present invention have a significant stability, at least about 10 N. More preferably, the digital tampons have a stability of at least about 20 N, and most preferably, they have a stability of about 30 N to about 85 N. Tampons with a stability that is too low do not have sufficient dimensional stability to maintain their basic structure during insertion as a digital tampon; tampons with a stability which is too high can be perceived as being too stiff or hard to be comfortably inserted as a digital tampon.

While the applicator tampon is protected by the rigid applicator device and the applicator tampon need not as have high a degree of column strength as a digital tampon, applicator tampons do require dimensional stability (especially radial) to be acceptable for use. This dimensional stability provides assurance, for example, that the tampon will not prematurely grow and split its packaging material or become wedged in a tampon applicator.

The process of the present invention begins with an open structure. The open structure may be a nonwoven web, a mass of randomly or substantially uniformly oriented materials, such as fibers, foams, or particles, and the like. This mass is then manipulated to form a tampon blank.

A nonwoven web useful in the present invention can be formed in any manner desired by the person of ordinary skill in the art. For example, fibers can be opened and/or blended by continuously metering them into a saw-tooth opener. The blended fibers can be transported, e.g., by air through a conduit to a carding station to form a fibrous web. Alternatively, a mass of substantially randomly oriented fibers can be formed by opening and/or blending them, transporting them, as above, to a station to form, e.g., a teabag-type tampon blank. Further processes may employ oriented fibers in a fibrous tow.

The tampon blank can be further processed to form a tampon. In a tampon forming process, a web can be formed into a narrow, fibrous sliver and spirally wound to form a tampon blank. In addition, a liquid-permeable cover material can be wrapped around the tampon blank to substantially contain the fibrous absorbent portion of the tampon. Examples of the further processing of the webs are described in Friese et al., U.S. Pat. No. 4,816,100, and Schwankhardt, U.S. Pat. No. 5,909,884 (the disclosures of which are herein incorporated by reference).

The tampon may include a rounded or flat insertion end.

The tampon may include a withdrawal mechanism, typically a string.

These tampons may be produced in accordance with the general teaching of Friese et al., U.S. Pat. No. 6,310,269, and Leutwyler et al., U.S. Pat. No. 5,832,576. These apparatus and methods disclosed in these references are modified, as described below, to form the tampons of the present invention. In addition, the tampons having pressed helical grooves may also be produced in accordance with the general teaching of Neipmann et al., U.S. Pat. No. 2,798,260, Wolff et al., U.S. Pat. No. 3,422,496, and Schoelling, EP 1383453.

Figure 7:
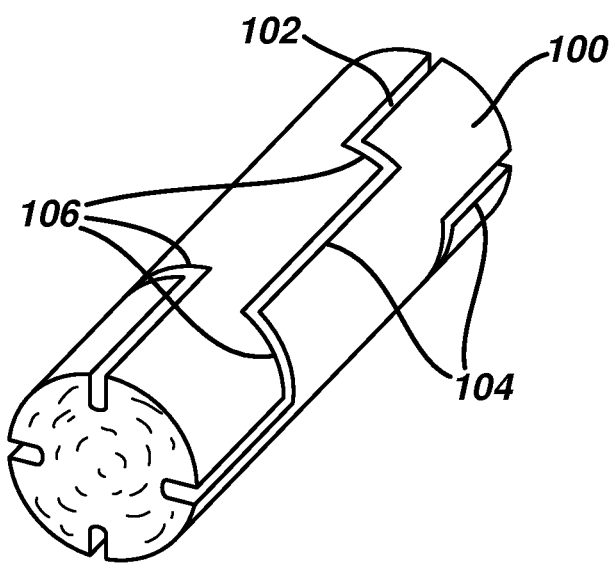
FIG. 7 shows a perspective view of still another alternate embodiment of a tampon of the present invention.

An apparatus for producing the simple, cylindrical, exemplary tampon shown in FIG. 7 is shown in FIGS. 8-13. The tampon 100 has four segmented grooves 102 having longitudinal segments 104 and accumulator segments 106.

Figure 8:
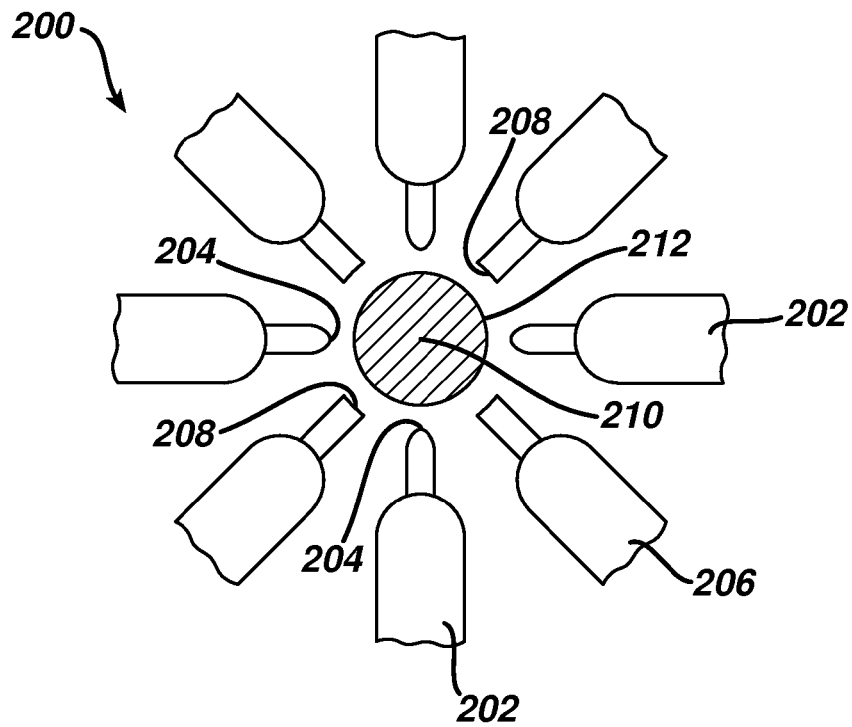
Figure 9:
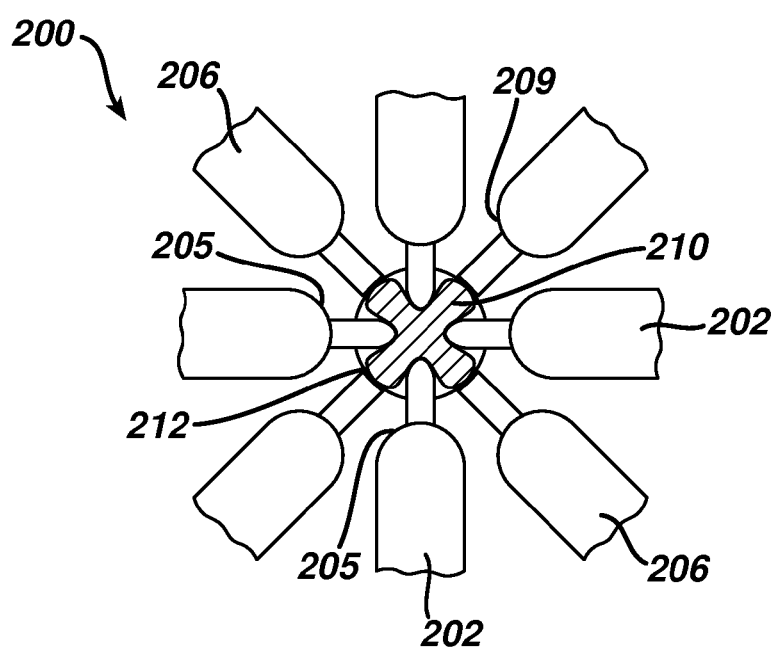

The apparatus 200 of FIGS. 8-13 includes two groups of altogether eight press dies arranged in a plane perpendicular to the press axis, the first group of press dies 202 has convex press faces 204 extending from press shoulders 205 and the second group of press dies 206 has concave press faces 208 extending from press shoulders 209. Initially, all press dies 202,206 are in the open position as shown in FIG. 8, and a tampon blank 210 is centered in the apparatus 200. As shown in FIG. 9, the press dies 202,206 converge to contact the outer surface 212 of the tampon blank 210 to hold it in place. However, the convex press faces 204 first group of press dies 202 immediately continue to press the tampon blank 210 to form segmented grooves that remain in the product of FIG. 7 as segmented grooves 102. The concave press faces 208 of the second group of press dies 206 then move radially inward toward the press axis to form the outer circumferential surface of the tampon as shown in FIG. 10. Finally, the first group of press dies 202 is withdrawn sufficiently to permit the compressed tampon to be ejected, as shown in FIG. 11.

Figure 12:
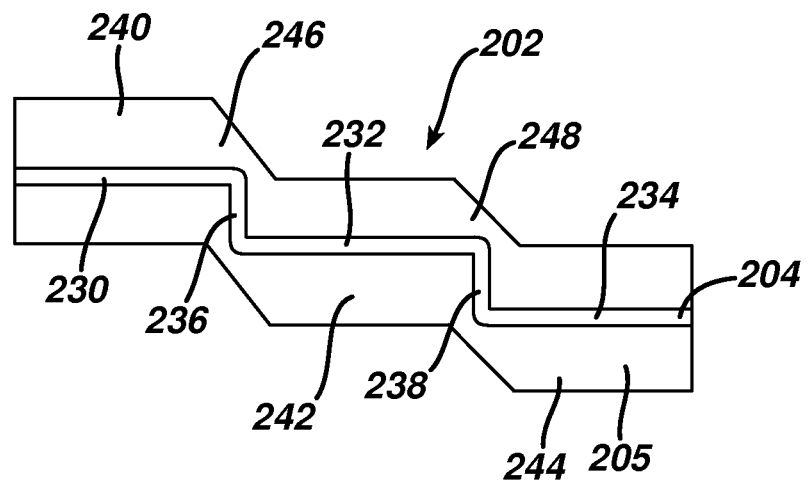
FIG. 12 is a view radially outward from the press axis showing one of the press dies of the tampon press of FIGS. 8-11.
Figure 13:
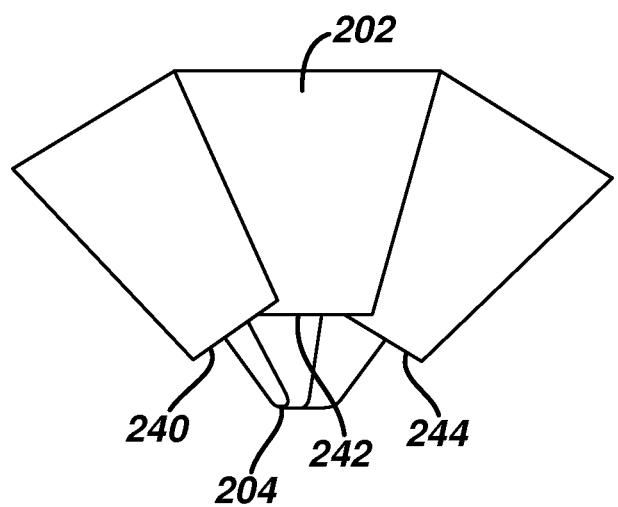
FIG. 13 is an end view of one of the press dies of the tampon press of FIGS. 8-11.

The first group of press dies 202 has groove-forming segments, shown in greater detail in FIGS. 12 and 13. FIG. 12 is a view radially outward from the press axis showing the convex press face 204 extending from the press shoulders 205. This particular embodiment includes three longitudinal press faces 230,232,234 joined by two circumferential accumulator press faces 236,238. The press shoulder 205 has three offset sections 240,242,244 to permit the step-wise orientation of the segmented groove. While this FIG. 12 shows the offset sections separated by angled sections 246,248, other transitions between offset sections would be apparent to the skilled practitioner.

FIG. 13 is an end view of a press die 202 illustrating an angular displacement of each of the offset sections 240, 242, 244 of the press shoulder 205. The second group of press dies 206 would have dimensions appropriate to fit between these adjacent press dies 202 of the first group.

As previously mentioned, tampons having step grooves may be made by modifying known methods. In particular, the method described in EP 1383453 discloses the use of individual press jaws and components to form helical grooves. By modifying the press jaws to include a step-forming pressing blade would result in a step-forming pressing surface. In this manner, it would be possible to form each step groove with a unitary jaw. Alternate methods may include a series of aligned jaws that each forms a portion of the step groove. For example, one a series of three jaws may be aligned such that one jaw forms the first ray and another jaw forms the third ray. By utilizing a third jaw to connect the first and third, the vertex would be formed.

What is claimed is:

1. An intravaginal tampon having an outer surface comprising an insertion end, a withdrawal end, and a center portion formed between the insertion end and the withdrawal end, the tampon having a longitudinal axis and formed of compressed material; wherein:
   a. at least two segmented grooves are formed in the outer surface and each segmented groove is separated from and spaced at a distance from an adjacent segmented groove; and
   b. each segmented groove has:
      i. at least one substantially longitudinal segment having a substantially longitudinal orientation; and
      ii. at least two accumulator segments having a substantially circumferential orientation such that each of the at least two accumulator segments have a major axis that run substantially circumferentially and intersects the at least one longitudinal segment at a vertex, wherein each of the respective intersections of the at least one substantially longitudinal segment and each of the at least two accumulator segments when measured from the vertex forms a step having a discernible angle of less than about 110°.

2. The intravaginal tampon of claim 1, wherein the at least one longitudinal segment is inclined with respect to the longitudinal axis.

3. The intravaginal tampon of claim 2, wherein the at least one substantially longitudinal segment has a helix angle of at least about 45°.

4. The intravaginal tampon of claim 3, wherein the at least one substantially longitudinal segment has a helix angle of at least about 75°.

5. The intravaginal tampon of claim 1, wherein at least one accumulator segment has a helix angle of less than about 25°.

6. The intravaginal tampon of claim 5, wherein at least one accumulator segment has a helix angle of less than about 10°.

7. The intravaginal tampon of claim 1, wherein the sum of the helix angle of the at least one substantially longitudinal segment and the helix angle of at least one accumulator segment is at least about 70°.

8. The intravaginal tampon of claim 7, wherein the sum of the helix angle of the at least one substantially longitudinal segment and the helix angle of at least one accumulator segment is at least about 90°.

9. The intravaginal tampon of claim 1, wherein:
   a. a first substantially longitudinal segment of a first of the at least two segmented grooves is connected to a second substantially longitudinal segment through a first accumulator segment;
   b. an adjacent, first substantially longitudinal segment of an adjacent segmented groove is connected to an adjacent, second substantially longitudinal segment through an adjacent, first accumulator segment;
   c. the first substantially longitudinal segment of the first segmented groove and the adjacent, first substantially longitudinal segment of the adjacent segmented groove are spaced at a first circumferential distance; and
   d. the second substantially longitudinal segment of the first segmented groove and the adjacent, second substantially longitudinal segment of the adjacent segmented groove are spaced at a second circumferential distance, different than the first circumferential distance.

10. The intravaginal tampon of claim 9, wherein the first accumulator segment extends generally from the first substantially longitudinal segment of the first segmented groove in a direction toward the adjacent segmented groove and the adjacent, first accumulator segment extends generally from the adjacent, first substantially longitudinal segment of the first segmented groove in a direction toward the first segmented groove.

11. The intravaginal tampon of claim 1, wherein adjacent segmented grooves have accumulator segments aligned generally circumferentially to provide a region having a first density that is greater than a second density in a region defined by the longitudinal segments.

12. The intravaginal tampon of claim 11, wherein the region having a first density has a longitudinal dimension of less than about 3 mm.

13. The intravaginal tampon of claim 1, wherein the intersecting at least one substantially longitudinal segment and at least one accumulator segment form a pooling region.

14. An intravaginal tampon having an outer surface comprising an insertion end, a withdrawal end, and a center portion formed between the insertion end and the withdrawal end, the tampon having a longitudinal axis and formed of compressed material; wherein:
   a. at least two segmented grooves are formed in the outer surface and each segmented groove is separated from and spaced at a distance from an adjacent segmented groove; and
   b. each segmented groove has:
      i. at least one substantially longitudinal segment having a substantially longitudinal orientation and having a first end disposed toward the insertion end of the tampon and a second end disposed toward the withdrawal end of the tampon; and
      ii. at least one accumulator segment having a first end disposed toward the withdrawal end of the tampon and joined at a discernible acute angle to the second end of the at least one substantially longitudinal segment and a second end, opposite the first end, wherein the second end of the accumulator segment is disposed toward the insertion end of the tampon.

15. The intravaginal tampon of claim 14, wherein the at least one longitudinal segment has a helix angle less than or equal to about 90° with respect to the longitudinal axis.

16. The intravaginal tampon of claim 15, wherein the at least one substantially longitudinal segment has a helix angle between about 45° to about 90°.

17. The intravaginal tampon of claim 16, wherein the at least one substantially longitudinal segment has a helix angle between about 75° to about 90°.

18. The intravaginal tampon of claim 14, wherein the at least one accumulator segment has a helix angle of less than about 25°.

* * * * *